United States Patent [19]
Mouaici

[11] Patent Number: 5,416,425
[45] Date of Patent: May 16, 1995

[54] SENSOR FOR DETERMINING ELECTRICAL CHARACTERISTICS OF A FLOWING LIQUID

[75] Inventor: Gérard Mouaici, Toulouse, France

[73] Assignee: Siemens Automotive S.A., Toulouse, France

[21] Appl. No.: 978,256

[22] Filed: Nov. 18, 1992

[30] Foreign Application Priority Data

Nov. 19, 1991 [FR] France ................ 91 14218

[51] Int. Cl.$^6$ .................... G01R 27/26; G01N 15/00
[52] U.S. Cl. ...................... 324/690; 73/61.43
[58] Field of Search ............. 324/690, 448, 686, 663; 73/61.44, 61.43

[56] References Cited

U.S. PATENT DOCUMENTS

| | | | |
|---|---|---|---|
| 2,892,976 | 6/1959 | Thayer | 324/330 |
| 4,543,191 | 9/1985 | Stewart et al. | 324/690 |
| 4,939,467 | 7/1990 | Noglami et al. | 324/663 |
| 5,005,402 | 4/1991 | Pischinger et al. | 73/61.43 |
| 5,231,358 | 7/1993 | Kapsokavathis et al. | 324/690 |

FOREIGN PATENT DOCUMENTS

| | | |
|---|---|---|
| 0379644 | 8/1990 | European Pat. Off. |
| 2409389 | 6/1979 | France |
| 3923992 | 1/1990 | Germany |
| 2149117A | 6/1985 | United Kingdom ............ 73/61.43 |
| 2210459 | 6/1989 | United Kingdom |

*Primary Examiner*—Maura K. Regan
*Attorney, Agent, or Firm*—Hill, Steadman & Simpson

[57] ABSTRACT

A sensor for measuring dielectric constant or resistivity of a flowing liquid, and especially of fuel mixtures for determining alcohol content, includes an inner tube through which the liquid flows, an outer sleeve about the inner tube in coaxial relation, holes in the inner tube to provide fluid communication at two locations to the space between the tube and the sleeve, and a partial restriction in the tube to divert some of the fluid flow into the space between the tube and the sleeve. The tube forms the inner electrode of a capacitor and the sleeve forms the outer electrode of the capacitor to measure dielectric constant. The ends of the sleeve are sealed in liquid tight fashion.

3 Claims, 1 Drawing Sheet

SENSOR FOR DETERMINING ELECTRICAL CHARACTERISTICS OF A FLOWING LIQUID

BACKGROUND OF THE INVENTION

1. Field of the Invention

The present invention relates generally to a sensor for measuring a dielectric constant or a resistivity of a flowing liquid and, in particular, is useful for determining ethanol content of a fuel mixture consisting of hydrocarbons and ethanol.

2. Description of the Related Art

As a fuel for internal combustion engines, it is known to mix relatively large amounts of alcohols, such as methanol and/or ethanol, with hydrocarbons. To obtain the maximum efficiency with a minimum of pollution when using such alcohol-based fuels, the engine settings should vary as a function of the fuel composition. Accordingly, it is known to control the engine settings depending upon the fuel composition.

It is known that the dielectric constant of a hydrocarbon/alcohol fuel mixture depends upon the composition of the mixture, and that the dielectric constant varies in an approximately linearly relationship with the alcohol content of the mixture. Various apparatus have been proposed based upon this characteristic.

German published application 39 23 992 discloses a sensor including a capacitor formed of a solid cylindrical central electrode and a hollow cylindrical peripheral electrode which is located coaxially about the central electrode. The two electrodes are placed in a chamber through which flows a fuel mixture. The fuel flow is perpendicular to the axis of the electrodes and the outer electrode is provided with two diametrically opposed longitudinal slots which enable the fuel mixture to pass between the electrodes. The disclosed sensor is quite complicated and, if it desired to not introduce an undesirable pressure drop in the flow of the mixture, the sensor must be quite large.

German published application 38 43 177 discloses a sensor that includes a metal tube through which flows a fuel mixture. The metal tube forms an outer electrode of a capacitor and a solid cylinder held in an axial position by centering elements forms a central electrode of the capacitor. The tube which forms the axial electrode is closed by insulating plugs. The connection of the central electrode traverses one of the plugs and the mixture enters and leaves the tube via transverse passages. Not only is the disclosed sensor complicated, but it is also bulky if an excessive pressure drop in the fuel flow is to be avoided.

SUMMARY OF THE INVENTION

An object of the present invention is to provide a simple sensor for measuring flowing fluids which is simple and inexpensive and which is less bulky compared to known sensors that have the same pressure drop through the sensor. In other words, for a sensor of the same size the present sensor offers less restriction in the fluid flow.

These and other objects and advantages of the invention are achieved in a sensor for determining the dielectric constant and the resistivity of a flowing liquid, the sensor including an outer metal tube or sleeve through which the liquid flows, the tube or sleeve forming an outer electrode of a capacitor. A cylindrical inner member is mounted coaxial with the outer metal tube and constitutes an inner or central electrode of the capacitor. The two electrode elements are mounted so that liquid flows in the space between the electrodes so that the electrical characteristics of the fluid may thereby be determined. Insulating plugs provided at the ends of the outer metal tube hold the two electrodes in a coaxial relative position. A particular feature of the invention is that cylindrical central or inner electrode is itself tubular and is connected at a first end to a liquid inlet and at a second end to a liquid outlet. In other words, the inner electrode is connected in a fuel line. Openings are formed in the walls of the inner electrode at two locations near each of the two insulating plugs to enable the liquid to flow into and through the space between the electrodes. Within the inner electrode at a position between these two opening locations is provided means for limiting but preferably not stopping the direct passage of the liquid from one end of the central electrode to the other.

The means for limiting the direct passage of the liquid from one end of the inner electrode to the other end results in the liquid being constantly replenished in the space between the two electrodes at a rate appropriate to the circumstances. Variations in the composition of the liquid as it flows though the sensor are thereby monitored. It is generally easy to calculate the cross section of the flow space between the two electrodes to ensure that the apparatus does create an additional pressure drop in the liquid flow yet also ensure that the size of device is kept relatively small. In particular, the outer electrode is of a diameter that is only slightly greater than the diameter of the inner electrode, and the inner electrode is formed from a tube of identical size to the supply and outlet lines for the liquid.

The present apparatus is relatively easy to manufacture since the steps necessary for making the device is limited to forming the openings in the central electrode and installing a fluid limiting means in this electrode, which can be performed very simply either by narrowing a region of the tube using a press or by force fitting a ring or other obstruction into the tube at a chosen location. The outer electrode is then easily mounted thereover. Electrical contacts are also established very simply with the present invention since the two electrodes are both easily accessible. In particular, clamping collars may be provided as the electrodes or soldered connections may be provided thereon.

The present invention therefore provides a very simple and low cost structure which is also effective for use in measuring the electrical characteristics of the flowing liquid as the liquid flows therethrough.

To further simplify the construction of the invention, provision is made in one embodiment for the outer electrode to have, close to each one of its ends, an annular narrowed region into which a flexible extension of the respective insulating plug is snap fitted to hold the plug in place. The inner electrode of this embodiment has in the vicinity of the respective insulating plugs an enlarged region which prevents axial displacement of the plug and, thus, of the outer electrode along the inner electrode. The space between the two electrodes is sealed by these plugs, and O-rings may be provided for additional leakage protection.

DETAILED DESCRIPTION OF THE PREFERRED EMBODIMENTS

Figure 1:
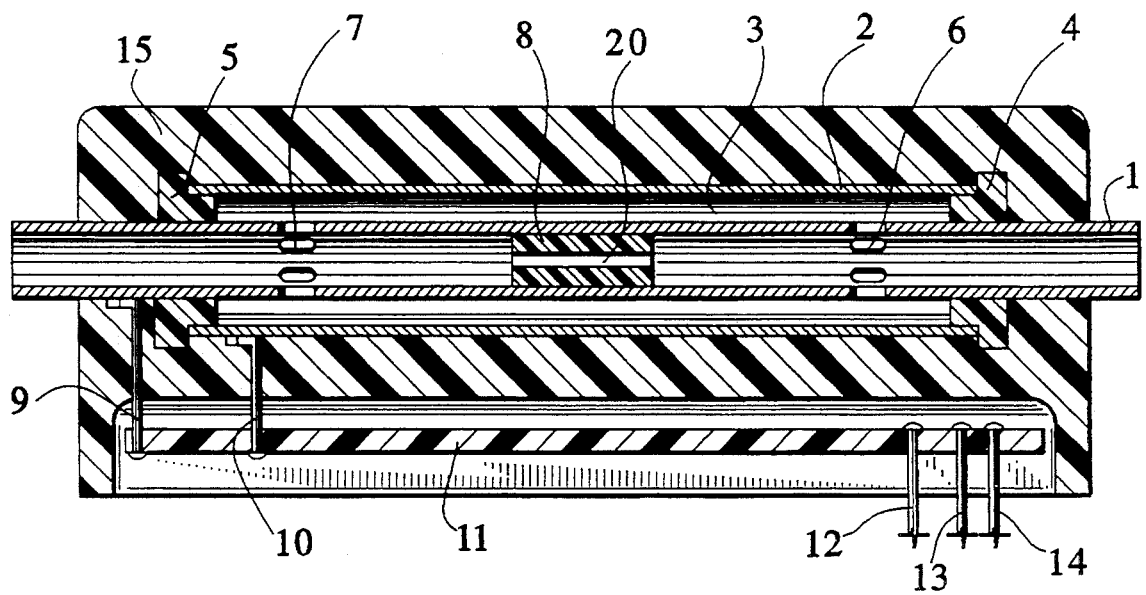
FIG. 1 is a diagrammatic axial section of an apparatus in accordance with the principles of the present invention.

In FIG. 1 is shown a metal tube 1 of the type which forms the usual gasoline or other fuel supply lines in a motor vehicle. Here, the metal tube 1 constitutes an inner electrode of a capacitor formed by the present sensor. A second metal tube 2 is mounted coaxially with the first metal tube 1 and is of a slightly greater diameter. The second metal tube 2 forms an outer electrode of the capacitor. An annular space 3 is formed between the tubes 1 and 2 and is limited at the ends of the outer tube 2 by two insulating and liquid-tight plugs 4 and 5. The plugs 4 and 5 are, for example, of a plastic or rubber material.

An arrangement of radial perforations 6 and 7 extend through the walls of the inner tube 1 in the regions near the end plugs 4 and 5 but within the space defined by the plugs 4 and 5. The radial perforations 6 and 7 provide fluid communication between the interior of the inner tube 1 and the annular space 3 between the two tubes 1 and 2. By providing the perforations 6 at two locations, the liquid flowing into the inner tube 1 may flow into and through the annular space 3 and then back into the inner tube 1 through the other set of perforations 6. The liquid flow path through the inner tube 1 is reduced by a restriction which in the first embodiment is a ring 8 that is forced fitted into the inner tube 1 between the two series of radial perforations 6 and 7. The ring has a central opening 20 through which a portion of the liquid flows.

A capacitance measurement between the inner and outer electrodes 1 and 2 results in finding the dielectric constant of the liquid in the annular space 3. Since the liquid flowing through the annular space 3 is constantly being replenished, the dielectric measurement reflects the current composition of the fuel flowing through the device.

Figure 2:
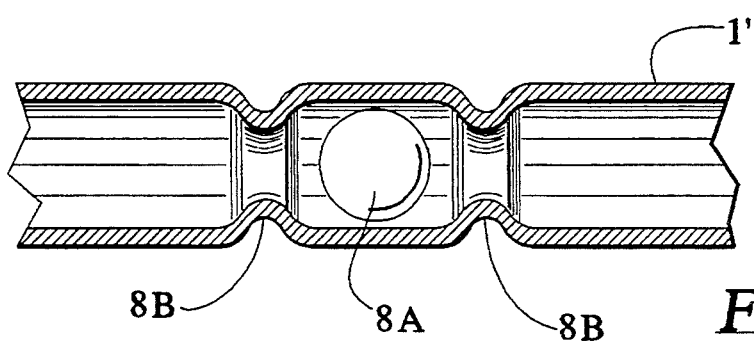
FIG. 2 is an axial section of a central tube portion similar to that shown in FIG. 1 illustrating an alternate embodiment of means for limiting direct passage of the liquid through the central tube.

In a second embodiment illustrated in FIG. 2, the ring 8 is replaced by a ball 8A which is inserted into the inner tube 1'. The ball 8A is small enough to provide a clearance between the ball 8A and the inside of the inner tube 1' yet still provide the desired restriction of the flow path. The ball 8A is held in place by two narrowed regions 8B, one preferably on either side of the ball 8A, formed in the tube 1'. At least one of the narrowed regions 8B is located downstream of the ball 8A in the flow direction. The restrictions 8B must not be circular so as not to form a shutoff valve that stops all flow through the inner tube 1'. The restrictions 8B are form by pinching or pressing the tube 1'.

Figure 4:
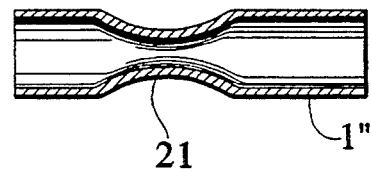
FIG. 4 is an axial section similar to FIG. 2 showing yet another embodiment of a means for limiting liquid flow through the central tube.

A third embodiment of the means for limiting or restricting is shown in FIG. 4, in the form of a narrowing 21 the inner tube 1''. The narrowing 21, formed by pinching the tube 1'', reduces the cross section available for the flow path and thereby restricts the flow therethrough.

Using the restriction of the ring 8 of FIG. 1, the restriction of the ball 8A of FIG. 2 or the restriction of the narrowing of FIG. 4, the tube 1 is connected at a first end to a fuel inlet pipe (not shown) and at the second end to a pipe for conveying fuel to an engine (not shown). In other words, the sensor is connected in the fuel line to the motor. Due to the restriction 8, 8A or 21, the liquid fuel flow is split within the present device into two portions. A first portion proceeds directly through the restriction 8, 8A or 21 while a second portion flows through the perforations 6 and 7 and along the annular chamber 3. The fuel flowing through the annular space 3 is thus of the same composition as the overall fuel flow through the present device. The fuel flow through the restriction is to prevent any pressure loss as a result of the diversion through the annular chamber 3.

It is to be understood that the restriction 8, 8A or 21 is to partially restrict the fuel flow through the inner tube 1. If the restriction 8, 8A or 21 is insufficiently effective, a major portion of the fuel flow will proceed through the restriction and thus the replenishment of the fluid in the annular space 3 will be slow and the fuel in the annular chamber 3 will not reflect changes in the composition of the fuel passing through the device. This results in the measurement of the capacitance through the fluid through the annular space 3 not accurately reflecting the current constituency of the fuel. In contrast, if the restriction 8, 8A or 21 is too pronounced relative to the annular space 3, the present device will create an undesirable drop in the pressure of the fuel flow. Making the outer tube 2 sufficiently large to eliminate the pressure drop makes the entire apparatus more bulky than necessary.

Connection strips 9 and 10 are welded to the apparatus, the connection strip 9 being welded to the inner tube 1 at a portion extending beyond the end plugs 4 or 5 and the connection strip 10 is welded to the outer tube 2. The connection strips 9 and 10 connect the two tubes 1 and 2, respectively, to an electronic circuit board 11 upon which is mounted electrical circuitry for shaping signals corresponding to variations in alcohol content of the fuel as a result of capacitance measured between the inner tube 1 and the outer tube 2. The corresponding electronic circuits are known and are within the scope of a person skilled in the art and are, accordingly, not described herein. Connections 12, 13, and 14 connect the circuitry of the circuit board 11 to devices outside the present apparatus, for example, an engine controller. A protective casing 15 of plastic or other non-conducting material encloses the entire apparatus.

Figure 3:
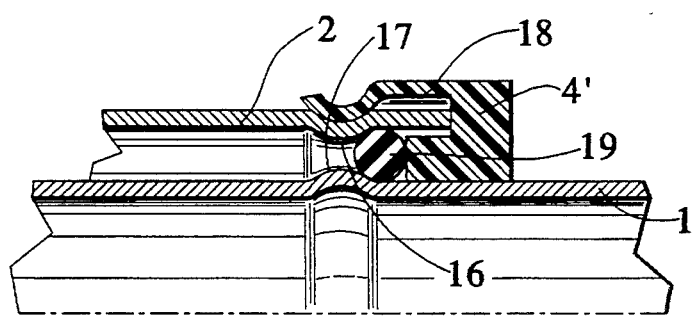
FIG. 3 is an enlarged detailed section illustrating an embodiment of an insulating plug according to the invention.

Referring to FIG. 3, a detailed view of an insulating plug 4' is shown. The outer tube 2 has, in the vicinity of one its ends, an annular narrowed region 16 formed therein. The inner tube 1 has, at the same position, an enlarged outwardly extending annular region 17. The insulating plug 4' includes a series of clips 18 molded in one piece with the plug and dimensioned so as to snap fit into the narrowed region 16 of the outer tube 2 when the plug 4 is brought to bear in the end of the tube 2. An O-ring seal 19 is wedged between the internal face of the narrowed region 16 and the external face of the enlarged region 17 so that the internal and external walls defining the interior space 3 are sealed in a liquid tight manner. The body of the plug 4' presses the O-ring seal 19 into place and holds it there.

Construction of the present invention is extremely simple with the illustrated embodiment. After the outer tube 2 is slipped over the inner tube 1, the O-ring seal 19 is installed between the two tubes 1 and 2, which insures centering of the tubes relative to one another. The plug 4' is pushed into the end of the outer ring tube 2 until the clips 18 extend into the narrowed region 16, thereby sealing the end of the tube 2. An opposite plug 5 at the other end of the outer tube 2 is installed in the same manner.

In the case where the inner tube 1 has, as is often the case, an enlarged region at one end for connection to another tube, the plug 4 may be made in two portions which are then assembled together by screwing or otherwise fastening the portions together. The O-ring seal 19 is preferable embedded between the two tubes to insure a liquid tight connection.

An alternate embodiment of the end plugs 4 and 5 replaces the clips 18 by a continuous flexible skirt of the same cross section which extends into the depression 16 to hold the plugs 4 and 5 in place.

The apparatus as shown herein is for use in monitoring alcohol content of a fuel mixture by measuring a dielectric constant of the flowing fluid. Persons skilled in the art will understand that the present apparatus can be used for determining composition variations of a liquid by determining electrical resistivity of the liquid.

To improve the accuracy of fluid composition determinations, it is possible to add to the present apparatus a means for determining the temperature of the flowing liquid. For example, one of the connection strips 9 or 10 may be folded back in the vicinity of the corresponding tube 1 or 2 to form a small tube inside which a thermistor or thermocouple welded joint is housed. It is thus possible to obtain a determination of the temperature at the actual location where the electrical parameter (the dielectric constant or resistivity) is being measured.

Although other modifications and changes may be suggested by those skilled in the art, it is the intention of the inventor to embody within the patent warranted hereon all changes and modifications as reasonably and properly come within the scope of his contribution to the art.

I claim:

1. A sensor for determining electrical characteristics of a flowing liquid, comprising:
    an electrically conductive tube connected in a fluid flow line so that liquid flows through said electrically conductive tube, said electrically conductive tube defining openings at two locations along said electrically conductive tube;
    an electrically conductive sleeve mounted coaxially about said electrically conductive tube to define a space therebetween, said electrically conductive sleeve enclosing said two locations of said openings;
    means for closing said electrically conductive sleeve at two locations on opposite sides of said two locations of said openings; and
    means for restricting liquid flow through said electrically conductive tube at a location between said two locations of said openings, said means for restricting leaving a partial flow path open through said electrically conductive tube so that a portion of liquid flowing through said sensor flows past said means for restricting and another portion of said liquid flows through said space between said electrically conductive tube and said electrically conductive sleeve, said means for restricting liquid flow comprising a narrowed region of said electrically conductive tube.

2. A sensor for determining electrical characteristics of a flowing liquid, comprising:
    an electrically conductive tube connected in a fluid flow line so that liquid flows through said electrically conductive tube, said electrically conductive tube defining openings at two locations along said electrically conductive tube;
    an electrically conductive sleeve mounted coaxially about said electrically conductive tube to define a space therebetween, said electrically conductive sleeve enclosing said two locations of said openings;
    means for closing said electrically conductive sleeve at two locations on opposite sides of said two locations of said openings; and
    means for restricting liquid flow through said electrically conductive tube at a location between said two locations of said openings, said means for restricting leaving a partial flow path open through said electrically conductive tube so that a portion of liquid flowing through said sensor flows past said means for restricting and another portion of said liquid flows through said space between said electrically conductive tube and said electrically conductive sleeve, said means for restricting liquid flow comprising a ball inside said electrically conductive tube, said ball being of a size to provide a clearance between inside walls of said electrically conductive tube and a surface of said ball.

3. A sensor for determining electrical characteristics of a flowing liquid, comprising:
    an electrically conductive tube connected in a fluid flow line so that liquid flows through said electrically conductive tube, said electrically conductive tube defining openings at two locations along said electrically conductive tube;
    an electrically conductive sleeve mounted coaxially about said electrically conductive tube to define a space therebetween, said electrically conductive sleeve enclosing said two locations of said openings;
    means for closing said electrically conductive sleeve at two locations on opposite sides of said two locations of said openings; and
    means for restricting liquid flow through said electrically conductive tube at a location between said two locations of said openings, said means for restricting leaving a partial flow path open through said electrically conductive tube so that a portion of liquid flowing through said sensor flows past said means for restricting and another portion of said liquid flows through said space between said electrically conductive tube and said electrically conductive sleeve,
    wherein said electrically conductive sleeve has an annular narrowed region adjacent at least one end,
    wherein said electrically conductive tube has an annular enlarged region opposite said annular narrowed region of said electrically conductive sleeve tube, and
    wherein said means for closing includes an extension engaging in said annular narrowed region of said electrically conductive sleeve when said means for closing closes said at least one end of electrically conductive sleeve.

* * * * *